(12) United States Patent
Althabit

(10) Patent No.: US 10,849,716 B2
(45) Date of Patent: Dec. 1, 2020

(54) DENTAL ISOLATOR FOR PROTECTING THE TONGUE AND CHEEK DURING DENTAL TREATMENT

(71) Applicant: Huda Othman Althabit, Riyadh (SA)

(72) Inventor: Huda Othman Althabit, Riyadh (SA)

( * ) Notice: Subject to any disclaimer, the term of this patent is extended or adjusted under 35 U.S.C. 154(b) by 413 days.

(21) Appl. No.: 15/568,058

(22) PCT Filed: Nov. 27, 2015

(86) PCT No.: PCT/SA2015/000015
§ 371 (c)(1),
(2) Date: Oct. 20, 2017

(87) PCT Pub. No.: WO2016/171593
PCT Pub. Date: Oct. 27, 2016

(65) Prior Publication Data
US 2018/0140380 A1    May 24, 2018

(30) Foreign Application Priority Data
Apr. 23, 2015   (SA) .................................. 115360494

(51) Int. Cl.
*A61C 5/90*   (2017.01)
*A61C 17/06*   (2006.01)
(Continued)

(52) U.S. Cl.
CPC ................ *A61C 5/90* (2017.02); *A61C 17/06* (2019.05); *A61B 13/00* (2013.01); *A61C 17/04* (2013.01); *A61F 13/2008* (2013.01)

(58) Field of Classification Search
CPC ............ A61C 5/90; A61C 17/06; A61C 17/00; A61C 17/10; A61C 17/092; A61B 13/00; A61F 13/2008
See application file for complete search history.

(56) References Cited

U.S. PATENT DOCUMENTS 2,613,441 A * 10/1952 Biggs .................. A61F 13/2008
433/136
2,885,783 A    5/1959 Golden
(Continued)

OTHER PUBLICATIONS

International Search Report issued in connection with PCT Application No. PCT/SA2015/000015 dated Mar. 29, 2015.

*Primary Examiner* — Tarla R Patel
(74) *Attorney, Agent, or Firm* — Steven M. Shape; Dennemeyer & Associates, LLC

(57) ABSTRACT

An isolating retractor instrument to protect a tongue and a cheek of a patient during a dental treatment. The isolating instrument includes a first isolating pad (A) for the tongue, and a second isolating pad (B) for the cheek. Each of the first isolating pad and the second isolating pad having a first (1) layer contacting and adhering to oral tissue, the first layer including an absorbing material for absorbing liquids, a second layer (2) including a fast-absorbing material which absorbs the liquids and holds the liquids, a third layer (3) adjacent the second layer, the third layer (3) including a reinforced, flexible material for supporting and stabilizing a respective isolating pad, and a fourth layer (4) including a reflective, smooth, flexible, and liquid-isolating material positionable to face a plurality of teeth of the patient. A flexible tape connects the first isolating pad and the second isolating pad.

5 Claims, 3 Drawing Sheets

Figure 1:
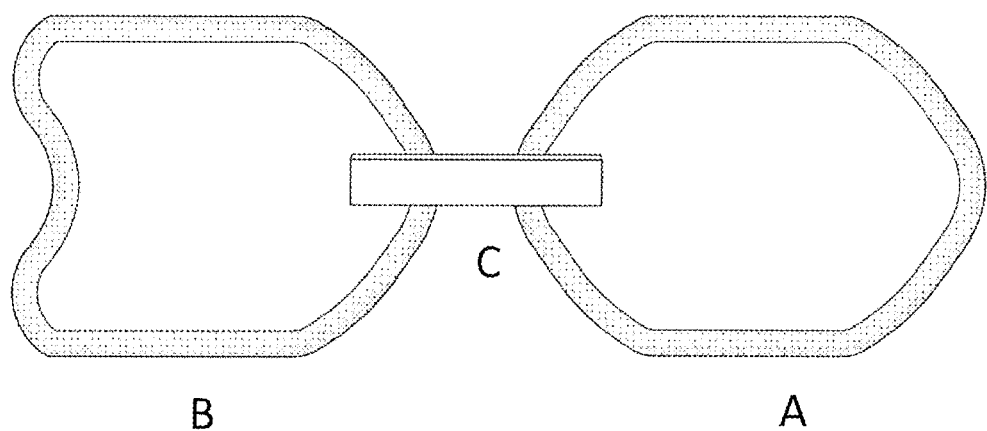

(51) Int. Cl.
   *A61B 13/00* (2006.01)
   *A61F 13/20* (2006.01)

(56) References Cited

U.S. PATENT DOCUMENTS

| | | | | |
|---|---|---|---|---|
| 3,468,030 | A * | 9/1969 | Nivison | A61F 13/2022 |
| | | | | 433/136 |
| 4,071,955 | A * | 2/1978 | Julius | A61F 13/2008 |
| | | | | 433/136 |
| 4,372,314 | A * | 2/1983 | Wall | A61F 13/2074 |
| | | | | 433/136 |
| 4,992,046 | A | 2/1991 | Sharp | |
| 5,071,349 | A * | 12/1991 | Skinner | A61C 5/90 |
| | | | | 433/136 |
| 5,499,917 | A * | 3/1996 | Erickson | A61C 5/82 |
| | | | | 433/137 |
| 5,749,729 | A * | 5/1998 | Skinner | A61F 13/2008 |
| | | | | 433/136 |
| 5,890,899 | A | 4/1999 | Sclafani | |
| 6,716,029 | B2 | 4/2004 | Fischer | |
| 8,182,264 | B2 * | 5/2012 | Dragan | A61C 5/90 |
| | | | | 433/140 |
| 8,535,056 | B2 * | 9/2013 | Dragan | A61B 1/0014 |
| | | | | 433/140 |
| 2006/0142718 | A1 * | 6/2006 | Maass, Jr. | A61F 13/12 |
| | | | | 604/370 |
| 2014/0330231 | A1 | 11/2014 | Zavala | |

* cited by examiner

DENTAL ISOLATOR FOR PROTECTING THE TONGUE AND CHEEK DURING DENTAL TREATMENT

BACKGROUND OF THE INVENTION

Field of the Invention

The present invention related to an isolating instrument for protecting the tongue and cheeks during dental treatment. This invention is one of the dentist instruments especially during dental treatments. It is adapted for the separation area between the cheeks and tongue to protect the patient from the risks of sharp dental instruments, also to provide for the dentist a dry and hygienic environment and easiness on dental treatments.

Relevant Technology

Considering the dental isolating instruments used currently and rampant in markets and dental clinics, we find the dental cotton rolls are the famous one, however these rolls do not give full protection for the cheeks or tongue and the dentist may need to change it many times. Another instrument used currently is dental rubber dam, which cannot be use in many cases due to the difficulties encountering the dentist while using it; in addition, some patients have allergic to it and wastes a lot of time to put it on, because it depends on other tools to hold it on the teeth which make the patient uncomfortable. One of the rubber dam examples is the U.S. Pat. No. 5,499,917.

U.S. Pat. No. 6,939,134, discover an instrument with two parts, the first part was a U-shaped enter inside the mouth to protect the cheeks and tongue, and the other part is outside the mouth as a handle; also the U.S. Pat. No. 2,831,480, with different design, an extra outer handle for the dentist to control it, which may obstruct his work and it may leads to injures and bruises in the soft tissue of the patient's mouth if using it a lot or hardly and does not give the full protection and covering to cheeks and tongue moreover does not provide a dry environment for dental procedure.

U.S. Pat. No. 6,716,029 is a tongue guards with bit block used in opens the patient mouth and it can only protects the tongue, and does not provide dry environment for the dental procedures.

U.S. Pat. No. 2,885,783 is an instrument to hold the cotton rolls to provide a dry environment for the cheeks and tongue but it does not provide the full covering for them.

U.S. Pat. No. 4,992,046 is an mouth prop for isolating teeth with full coverage and absorbing the saliva but it working upon a preselected teeth only which is cannot treat the upper teeth and lower teeth at the same time, and it is a hard instrument not flexible which it be not comfortable to the patient.

U.S. Pat. No. 5,890,899 is a Dental isolator includes a prop stem for propping a patient's mouth open and a buccal member for displacing the patient's cheek from the right side of the mandibular arch of the patient. However, it lacks to giving the full coverage for the tongue and cheeks together, also it may cause bruises to the membranes that surrounding the mouth.

Through the above examples, comparing to the present invention, which they differ from each other of its own features and functions that lead to the necessity to provide an instrument with simpler design and has more features in using. This patent gives the full coverage and protection for the tongue and cheeks at the same time, and allows treating the upper and lower teeth and can be used for the right and left sides. In addition, it helps to provide a dry environment from saliva without causing bruises or injuries in oral soft tissues as well. Therefore, it helps to comfort the patient and the dentist Also; it gives the dentist more space to work easily.

SUMMARY OF THE INVENTION

In the view of the foregoing, this invention aims to provide a simple design instrument characterized by lightness and easiness use to achieve two things. First, for the patient, by comforting him and protecting the tongue and cheeks and other oral tissues from sharp dental instruments, also avoiding accidental swallow of dental materials. Second, for the dentist, by providing a dry environment, easy and comfortable controlling for treating the upper teeth and lower teeth with fewer risks and lesser time, as well it can use the instrument during dental treatment without needing to replace it and it is fit both sides of the mouth, right and left side.

Figure 2:
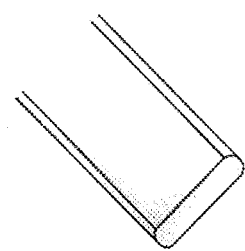

This goal achieves by an instrument consists of a flexible isolating pad with two sides (A) for the tongue, and a flexible isolating pad for the cheeks with two sides (B). Each one of them consists of saliva absorbing layer. This tow pads are connected by a flexible easy folding tape (C). This instrument characterized by borders that do not cause any bruises or injures to the soft tissue with one creative concept as explained below (FIG. 2).

BRIEF DESCRIPTION FOR THE FIGURES

This invention requires having descriptive figures help to understand the idea and explain the function of the invention.

FIG. 1: is a perspective view of an embodiment of the main parts of the instrument from one side.

FIG. 2: is a perspective view of an embodiment of the instrument's shape after folding to enter inside the mouth.

Figure 3:
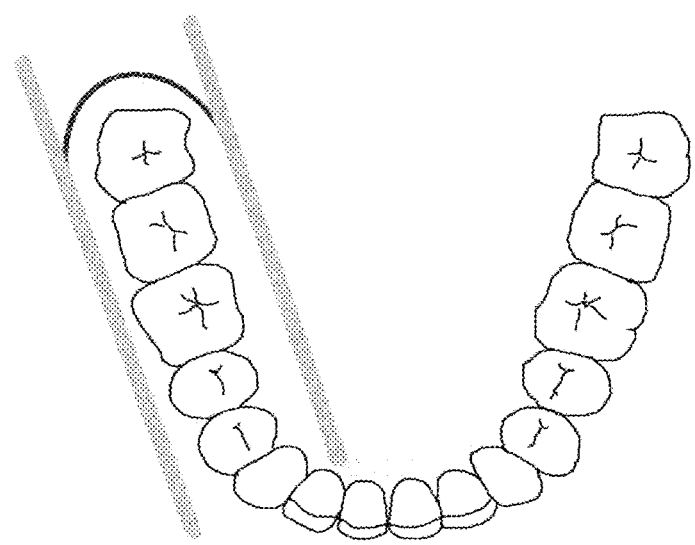

FIG. 3: is a top plan view of the instrument inside the patient's mouth.

Figure 4:
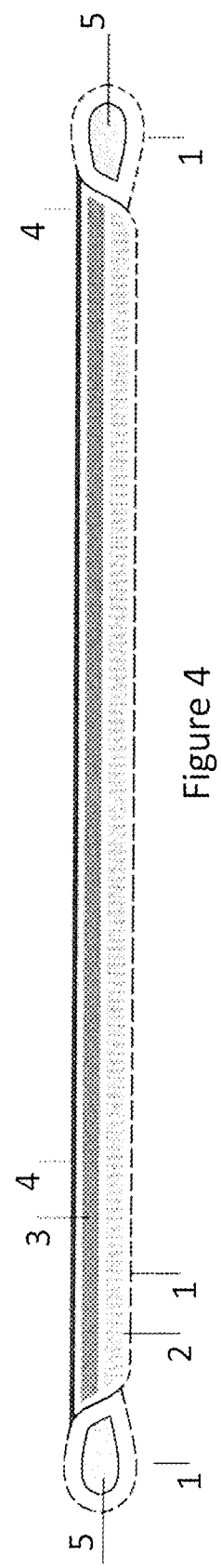

FIG. 4: a cross-sectional view of the isolating pad of the tongue (A), or isolating pad of the cheek (B), the layers forming the isolating pads for both (A) and (B).

Figure 5:
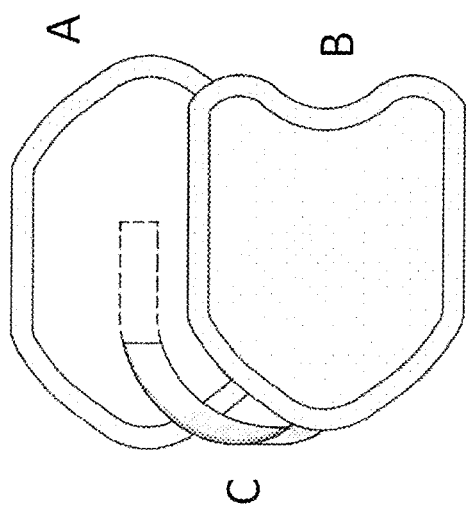

FIG. 5: a cross-sectional view of the tape (C) as in FIG. 1, describes the tapered edges of the tape.

Figure 6:
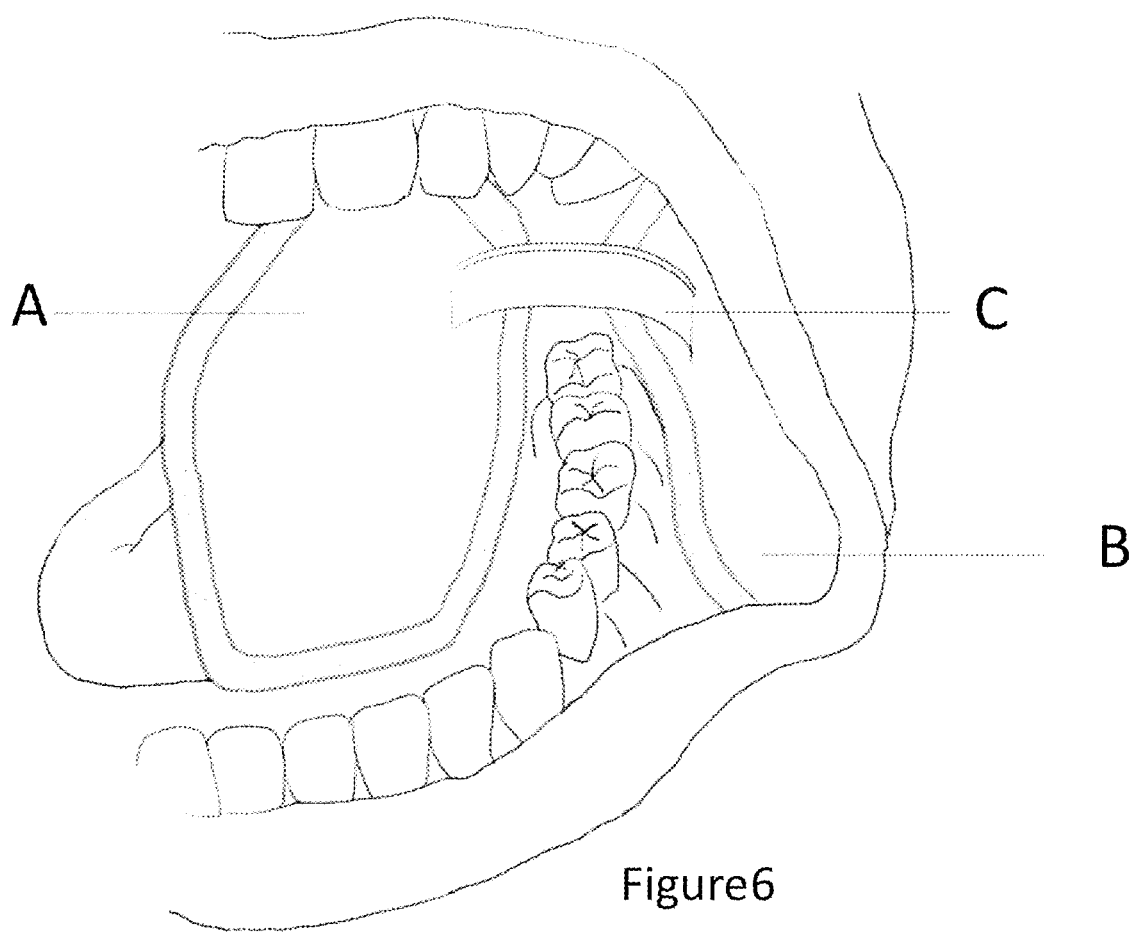

FIG. 6: an embodied view of the instrument inside the patient's mouth.

THE DETAILED DESCRIPTION

The idea of this invention lies in a simple and creative instrument with two flexible isolating pads connected with a flexible and folding tape. The two isolating pads entered inside the mouth in the place that should be treated, it allows the patient to close and open his mouth easily, and it uses for both sides of the mouth the right and left.

FIGS. 1 through 6 illustrate a retractor for protecting the tongue and cheeks during dental treatment. The first pad is adapted as an isolating covering for protecting the tongue (A), and the other pad is adapted as an isolating covering for protecting the cheek (B). Both isolating pads (A) and (B) have rounded edges (FIG. 2 and FIG. 4) to provide the protection for the mouth membrane from bruises and injuries.

In FIG. 1, the isolating pad (A) characterized in that has convex tips as shaped the internal oral cavity for giving full protection to the tongue, while the isolating pad (B) characterized in that has a convex internal tip and a concave external tip shapes at the internal lip border. As illustrated in FIG. 2 and FIG. 4, both isolating pads (A) and (B) characterized by having two sides. The internal side (1) adapted to adhere to the oral tissue, it is made of a material (such as cotton tissue) allows to adhere to oral tissue and helps to absorb the saliva or water from the oral cavity so it can stabilize the instrument and prevent it from moving. The other side (4) external at the dental operating area which is front of the teeth, is made of a smooth cardboard and has a reflected color (like white) to helps for reflecting the light, and gives protection to the area from sharp dental instruments.

FIG. 4 shows both isolating pads comprise of four layers. A first layer (1) which faces the mouth tissue is a thin layer of an absorbing material (like cotton) helps to adhere to the tissue and absorbs the saliva or liquids. A second layer (2) is a fast-absorbing material, it absorbs the saliva or liquids and can hold the fluids in a long time like the one used in diapers. Beside the second layer is a supportive layer (3) made of a reinforced flexible material (such as plastic) to support and stabilize the pad. Then a last layer (4) is a cardboard, which faces the teeth, is a smooth, a flexible, an isolating of the liquids and has a reflected color (like white). Each edge of the isolating pads is adapted to prevent the injuries of mouth tissue; it is a rounded and derive the supporting and stability from the extension of cardboard layer (4). These edges includes two layers; the first layer (1) is a thin absorbing material (such cotton) helps to adhere to the tissue and absorb the saliva or liquids, and the second layer (5) is a material which is unable to absorb the liquids or saliva (like a sponge silicon) to give the protection and stabilization for the isolating pad, smoothness for its borders.

FIG. 3 and FIG. 6, the tape (c), connected the two isolating pads (A) and (B), is a flexible foldable extending from the inside of the first isolating pad (A) and connects the other one (B) to provide the supporting and stability for both. It characterized by smooth convex edges to prevent any bruises or injures to the oral soft tissue as shown in FIGS. 2 and 5. Its width characterized by suiting the internal jaw's width to ease opening and closing the mouth while dental treatment as shown in FIGS. 3 and 6.

This instrument will have several sizes to suit the mouth of the children and adults. It is worth mentioning that everything similar either to explained here by figures or by description is meant to be under the invention.

The invention may be embodied in other specific forms without departing from the spirit or essential characteristics thereof. The described embodiments are to be considered in all respects as illustrative and not restrictive. Accordingly, the scope of the invention is indicated by the appended claims rather than by the foregoing description. All changes which come within the meaning and range of equivalents of the claims are to be embraced within their scope.

The invention claimed is:

1. An isolating instrument for protecting a tongue and inside of a cheek of a patient during a dental treatment, the isolating instrument comprising:
   a first isolating pad (A) positioned transversely over the tongue, and a second isolating pad (B), separated and perpendicular from the first isolating pad (A), for positioning inside of the cheek, each of the first isolating pad and the second isolating pad having flexibility and a rounded edge about an outer periphery of a respective isolating pad, each of the first isolating pad and the second isolating pad comprising:
      a thin first (1) layer contacting and adhering to oral tissue, the first layer comprising an absorbing material for absorbing liquids;
      a second layer (2) comprising a fast-absorbing material which absorbs the liquids and holds the liquids;
      a third layer (3) adjacent the second layer, the third layer (3) comprising a reinforced, flexible material for supporting and stabilizing a respective isolating pad of the first isolating pad and the second isolating pad; and
      a fourth layer (4) comprising a reflective, smooth, flexible, and liquid-isolating material positionable to face a plurality of teeth of the patient; and
   a flexible tape connecting the first isolating pad and the second isolating pad.

2. The isolating instrument according to claim 1, wherein the rounded edge comprises the first layer (1) adherable to the soft tissue and configured to absorb the liquids, the first layer at least partially surrounding an inner layer (5) comprising a material unable to absorb the liquids, the inner layer providing support and smoothness for the rounded edge.

3. The isolating instrument according to claim 2, wherein the inner layer (5) comprises a sponge silicon.

4. The isolating instrument according to claim 1, wherein the first isolating pad (A) comprises a convex tip configured to follow a profile of an internal oral cavity of the patient for providing protection to the tongue.

5. The isolating instrument according to claim 1, wherein the second isolating pad (B) comprises a convex internal tip and a concave external tip opposite the convex internal tip configured to follow a profile of an internal lip border of the patient.

* * * * *